(12) United States Patent
Fuerst et al.

(10) Patent No.: US 11,690,674 B2
(45) Date of Patent: Jul. 4, 2023

(54) MOBILE VIRTUAL REALITY SYSTEM FOR SURGICAL ROBOTIC SYSTEMS

(71) Applicant: Verb Surgical Inc., Santa Clara, CA (US)

(72) Inventors: Bernhard Fuerst, Sunnyvale, CA (US); Eric Johnson, Pacific Grove, CA (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 369 days.

(21) Appl. No.: 16/840,144

(22) Filed: Apr. 3, 2020

(65) Prior Publication Data
US 2021/0307831 A1   Oct. 7, 2021

(51) Int. Cl.
*A61B 34/10*   (2016.01)
*A61B 34/35*   (2016.01)
(Continued)

(52) U.S. Cl.
CPC .............. *A61B 34/10* (2016.02); *A61B 34/35* (2016.02); *A61B 34/37* (2016.02); *A61B 34/74* (2016.02);
(Continued)

(58) Field of Classification Search
CPC ......... A61B 34/10; A61B 34/35; A61B 34/37; A61B 34/74; A61B 34/76;
(Continued)

(56) References Cited

U.S. PATENT DOCUMENTS

| | | |
|---|---|---|
| 9,643,314 B2 | 5/2017 | Guerin et al. |
| 2009/0305210 A1 | 12/2009 | Guru et al. |

(Continued)

FOREIGN PATENT DOCUMENTS

| | | |
|---|---|---|
| WO | 2016149794 | 9/2016 |
| WO | 2019006202 | 1/2019 |

(Continued)

OTHER PUBLICATIONS

International Preliminary Report on Patentability for International Application No. PCT/US2019/064713 dated May 12, 2022, 6 pages.

(Continued)

*Primary Examiner* — Jitesh Patel
(74) *Attorney, Agent, or Firm* — Aikin & Gallant, LLP

(57) ABSTRACT

Mobile virtual reality system for simulation, training or demonstration of a surgical robotic system can include a virtual reality processor. The processor can generate a virtual surgical robot and render the virtual surgical robot on a display. The virtual surgical robot can include a virtual surgical tool. A handheld user input device (UID) can sense a hand input from a hand. A foot input device can sense a foot input from a foot. The virtual reality processor can be configured to control a movement or action of the virtual surgical robot based on the hand input, and change which of the virtual surgical instruments is controlled by the one or more handheld UIDs based on the foot input. Other embodiments and aspects are disclosed and claimed.

20 Claims, 6 Drawing Sheets

(51) Int. Cl.
*A61B 34/37* (2016.01)
*G06T 19/00* (2011.01)
*G02B 27/01* (2006.01)
*A61B 34/00* (2016.01)

(52) U.S. Cl.
CPC ............ *A61B 34/76* (2016.02); *G02B 27/017* (2013.01); *G06T 19/006* (2013.01); *A61B 2034/101* (2016.02)

(58) Field of Classification Search
CPC .... A61B 2034/101; A61B 2017/00115; A61B 2034/2048; A61B 2090/365; G02B 27/017; G06T 19/006
See application file for complete search history.

(56) References Cited

U.S. PATENT DOCUMENTS

| | | |
|---|---|---|
| 2010/0211897 A1 | 8/2010 | Cohen et al. |
| 2010/0234857 A1 | 9/2010 | Itkowitz et al. |
| 2013/0245375 A1 | 9/2013 | DiMaio et al. |
| 2014/0018960 A1 | 1/2014 | Itkowitz |
| 2016/0314710 A1* | 10/2016 | Jarc ................. G09B 23/28 |
| 2017/0049517 A1 | 2/2017 | Felder et al. |
| 2017/0319282 A1 | 11/2017 | Jarc et al. |
| 2018/0098813 A1 | 4/2018 | Nesichi et al. |
| 2018/0116724 A1* | 5/2018 | Gmeiner ............. B29C 35/02 |
| 2018/0280099 A1* | 10/2018 | Cone ................. B25J 13/04 |
| 2018/0324539 A1 | 11/2018 | Lovitt |
| 2018/0338806 A1 | 11/2018 | Grubbs |
| 2019/0005848 A1 | 1/2019 | Garcia Kilroy et al. |
| 2019/0279524 A1* | 9/2019 | Stoyanov ............. G16H 30/40 |
| 2019/0307510 A1 | 10/2019 | Rotenberg et al. |
| 2019/0318640 A1* | 10/2019 | Goel ................. A61B 90/36 |
| 2019/0325574 A1* | 10/2019 | Jin ................. G06V 20/41 |
| 2020/0038124 A1 | 2/2020 | Lin et al. |
| 2020/0074402 A1 | 3/2020 | Adato et al. |

FOREIGN PATENT DOCUMENTS

| | | |
|---|---|---|
| WO | 2019139935 | 7/2019 |
| WO | 2019148286 | 8/2019 |

OTHER PUBLICATIONS

Office Action for U.S. Appl. No. 16/667,237 dated Mar. 16, 2022, 5 pages.
International Search Report and Written Opinion for International Application No. PCT/US2019/064713 dated Jul. 21, 2020, 9 pages.
Non-Final Office Action for U.S. Appl. No. 16/667,237 dated Mar. 31, 2021, 17 pages.
Non-Final Office Action for U.S. Appl. No. 16/667,241 dated Apr. 27, 2021, 17 pages.
Non-Final Office Action for U.S. Appl. No. 16/870,586 dated Mar. 31, 2021, 21 pages.
Final Office Action for U.S. Appl. No. 16/667,237 dated Aug. 26, 2021, 17 pages.
International Search Report and Written Opinion for International Application No. PCT/US2020/031367 dated Dec. 23, 2020, 15 pages.
Non-Final Office Action for U.S. Appl. No. 16/667,237 dated Nov. 22, 2021, 14 pages.
Almusawi, A.J.R., et al., "Simulation in virtual reality: Robotic training and surgical applications," Scientia Iranica B (2019), 26(6), pp. 3369-3374.
International Preliminary Report on Patentability for International Application No. PCT/US2020/031367 dated Oct. 13, 2022, 6 pages.

* cited by examiner

MOBILE VIRTUAL REALITY SYSTEM FOR SURGICAL ROBOTIC SYSTEMS

TECHNICAL FIELD

This invention relates generally to surgical robotic systems, and more specifically to a mobile virtual reality system for simulation, training, or demonstration of a surgical robotic system and/or procedure. Other embodiments are described.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. Thus, a surgical robotic arm can assist in performing surgery.

Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

SUMMARY

It may be desirable, in one aspect, to use a virtual environment (e.g., virtual reality, mixed reality, or augmented reality) to simulate, train, or demonstrate a surgical robotic system and/or procedure. In this manner, medical staff (e.g., surgeons) can beneficially familiarize themselves with surgical robotic systems and procedures in a virtual environment, without the entire physical surgical robotic system (e.g., surgical robotic arms, platform, control station, operating room, etc.). The surgical robotic system and procedure can be simulated with a virtual reality system that mimics the physical surgical robotic system, including an immersive virtual environment (e.g., a 3-D display in a head worn device). Full-blown virtual reality systems can be bulky and require external sensors (e.g., cameras placed in one or more areas of a physical environment to detect and sense a user) that can make the set-up difficult. Such systems can also require wiring and routing of wires/cables. Thus, such systems are not mobile because they are difficult to move from one location to another. Thus, it is beneficial to provide a virtual reality system that is mobile (e.g., with minimal parts and set-up complexity) so that the system can be efficiently transported from one location to another, e.g., to train medical staff.

A mobile virtual reality can use real hardware and inside-out tracking to run fully realized patient simulations. Such systems can have no external trackers (e.g., cameras). Foot pedals or foot tracking (e.g. optically tracking a foot with sensors or inside-out cameras) can be designed into such a system. Simulation can be driven with real robot models that are indicative of the real surgical robotic system used in a real procedure. Such a system can be easily kitted and passed between medical staff for training.

In one aspect, a mobile virtual reality system for simulation, training or demonstration of a surgical robotic system, includes: a processor; a display, to receive and show a virtual virtual surgical robot, based on a data stream generated by the processor, the virtual surgical robot including a plurality of virtual surgical instruments; one or more handheld user input devices (UIDs), sensing a hand input from a hand; and one or more foot input devices, sensing a foot input from a foot. The processor can be configured to control a movement of the virtual surgical robotic system based on the hand input, and change which of the virtual surgical instruments is controlled by the one or more handheld UIDs.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosures.

Reference in the specification to "one embodiment" or "an embodiment" means that a particular feature, structure, or characteristic described in conjunction with the embodiment can be included in at least one embodiment of the disclosure. The appearances of the phrase "in one embodiment" in various places in the specification do not necessarily all refer to the same embodiment.

Figure 1:
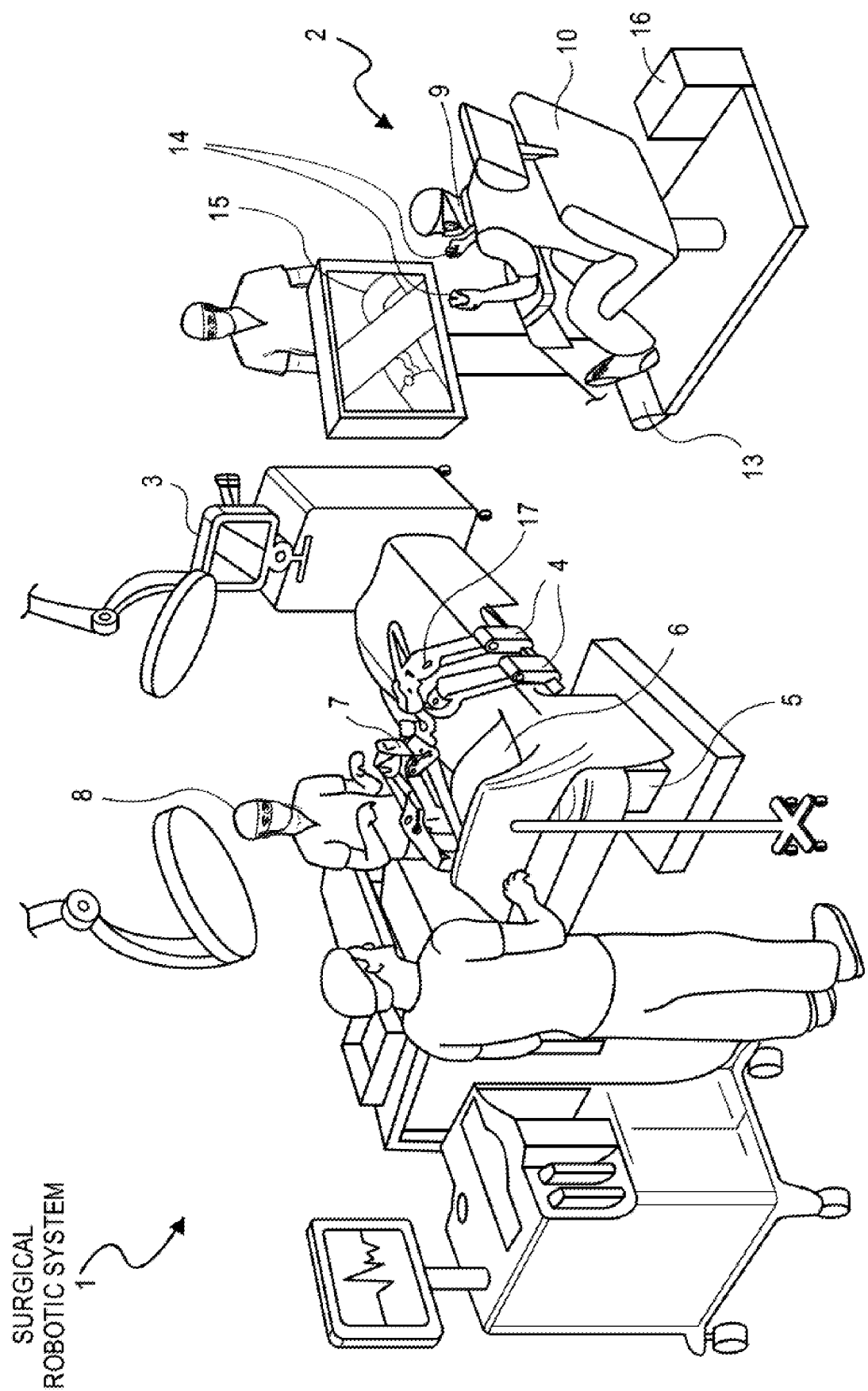
FIG. 1 illustrates a surgical robotic system according to one embodiment.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

A surgical robotic arm can have movable, jointed, and/or motorized members with multiple degrees of freedom that can hold various tools or appendages at distal ends. Example systems include the da Vinci® Surgical System which can be used for minimally invasive surgery (e.g., urologic surgical procedures, general laparoscopic surgical procedures, gynecologic laparoscopic surgical procedures, general non-cardiovascular thoracoscopic surgical procedures and thoracoscopically assisted cardiotomy procedures). A "virtual surgical robotic arm" can be a computer generated model of a robotic arm rendered over the captured video of a user setup. The virtual surgical robotic arm can be a complex 3D model of the real robotic arm. Alternatively, or additionally, a virtual surgical robotic arm can include visual aids such as arrows, tool tips, or other representation relating to providing pose information about a robotic arm such as a geometrically simplified version of the real robotic arm.

Mobile Virtual Reality System

Figure 2:
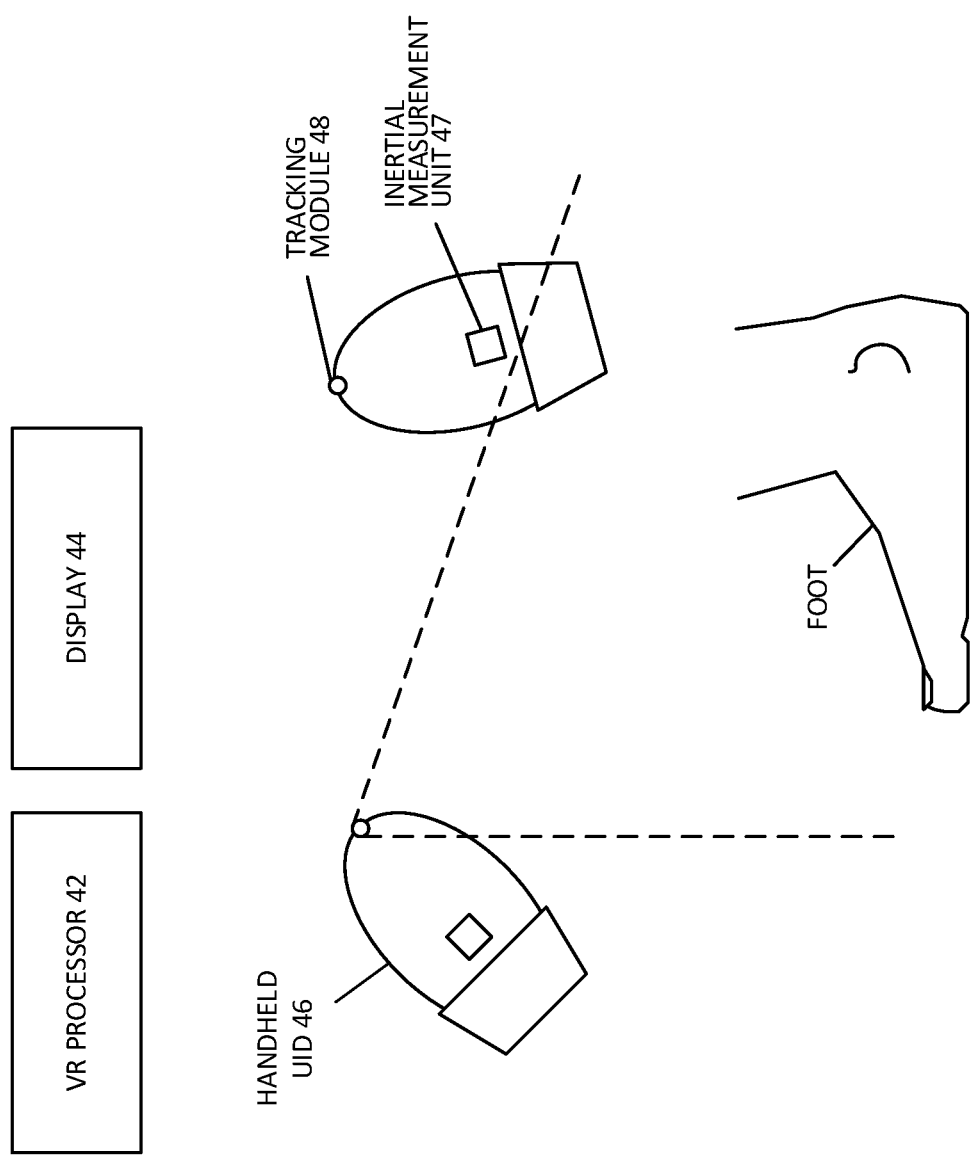
FIG. 2 illustrates a virtual reality system for simulation, training or demonstration of a surgical robotic system, according to one embodiment.

Referring to FIG. 2, a mobile virtual reality system 40 for simulation, training or demonstration of a surgical robotic system, can include: a virtual reality processor 42; a display 44, to receive and show a virtual reality environment generated by the processor, the virtual reality environment including a virtual surgical robotic system (e.g., the surgical robotic system shown in FIG. 1). In particular, the processor can generate a data stream that includes a virtual surgical robot (e.g., virtual replicas of one or more surgical robotic arms 4, and/or platforms 5 shown in FIG. 1) and one or more virtual surgical instruments (e.g. a virtual replica of a surgical tool 107 shown in FIG. 1). The virtual reality processor is configured to control a movement or action of the virtual surgical robot (including the instruments) based on the hand inputs, and actions commanded through sensors on the handheld controllers (UIDs) or foot input. For example, based on hand inputs, a virtual surgical robotic arm or tool in the virtual reality environment can move, thus simulating a real-life surgical procedure with the same or similar hand inputs. Feet inputs can change which of the virtual surgical instruments is controlled by the one or more handheld UIDs. For example, a foot input can switch control from one virtual surgical instrument that is attached to one virtual surgical robotic arm, to another virtual surgical instrument that is attached to another virtual surgical robotic arm. In other cases, foot inputs can toggle control between different virtual robotic arms or between members of the same virtual robotic arm. In other words, with foot inputs, a user can toggle between which equipment member is active in being controlled by the hand inputs. In some embodiments, a foot input can act as a clutch that pauses control of the virtual surgical robot (including one or more arms and instruments). For example, when a foot input indicates that a foot is depressing a foot pedal, all inputs from the handheld UID would be ignored. When the foot input indicates that the foot pedal is released, then control of the virtual surgical robot can resume in a position prior to activation of the clutch. In one embodiment, various devices can communicate over a network (e.g., the handheld input, the processor, the foot input, and the display). The network can be wired or wireless, and can use known communication protocols (e.g., TCP/IP, CAN, RS-232, etc.).

In one embodiment, the mobile virtual reality system does not include external stationary components of a tracking system (e.g. camera). Beneficially, no components of a tracking system would be required to be installed in simulation rooms, which can cut down on the time to prepare surgical simulations. No external components of a tracking system also provide for a more compact and mobile virtual training system. Instead of external components, the system can utilize built-in tracking devices, such as inside-out cameras, or cameras mounted on laptops or head worn devices, as discussed in other sections.

In one embodiment, the processor and the display are integral to a computer, such as a laptop. In one embodiment, the display is a two-dimensional screen or a three-dimensional screen (e.g., multiview 3D display, volumetric 3D display, or digital hologram display). In one embodiment, the display is a 3D wearable display, worn on a user's head. The processor can be integral with the display with or without requiring an external computer (e.g., housed in a device such as a laptop or a head worn computing device).

Handheld Input

The mobile system can include one or more handheld user input devices (UIDs) 46 that can sense a hand input from motion of a hand. For example, a user's hand can squeeze, rotate or translate the UID. These hand inputs can be sensed by the UIDs.

In one embodiment, as shown in FIG. 2, the one or more handheld UIDs 46 contain an inside-out tracking module 48 and/or an inertial measurement unit (IMU) 47. The inside-out tracking module 48 can include one or more cameras or other sensors capable of mapping objects and movements thereof outside of the UIDs. The inside-out tracking module 48 can have different locations on the UID, such as, but not necessarily, at a front location of the handheld UID (as shown in FIG. 2) away from where the UID is held. Images from the one or more cameras or sensors can be processed to determine movements and position of the UID, which can be used to control the virtual surgical robotic system. The IMU 47 can include an accelerometer, a gyroscope, or combinations thereof. In one embodiment, the UIDs can include one or more switches to squeeze, and/or one or more buttons. In one embodiment, the processor is configured to determine the hand input (e.g., movement, position, translation, or orientation of the UID) based on inputs from the inside-out tracking module (e.g., a camera), and/or the IMU.

Foot Input

The mobile system can include one or more foot input devices, sensing a foot input from one or more feet. The foot input devices can come in different forms. In one embodiment, FIG. 3A shows an optical sensor or external camera 52 to capture visual data containing the foot input. A processor, e.g. the VR processor 42 or a dedicated foot input processor can be configured to determine the foot input based on recognizing and tracking a movement, position, or orientation of the foot (e.g., with machine learning and/or a trained neural network).

In one embodiment, the optical sensor or tracking module 48 can include a camera housed in the one or more handheld UIDs 46, as shown in FIG. 2. The camera can have a wide angle view or lens, e.g. capable of viewing 170° or greater, to capture the visual data containing the foot input from hand-held positions. Thus, in such an embodiment, the system can obviate the need for separate foot input hardware because the handheld UIDs and inside-out tracking modules therein can synergistically be used to sense foot inputs.

Figure 3B:
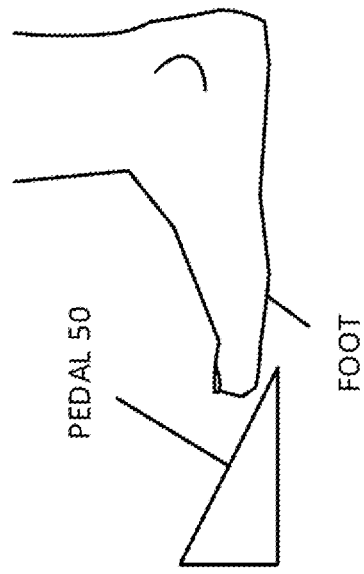
FIGS. 3A-3C illustrate foot input means, according to various embodiments.
Figure 3C:
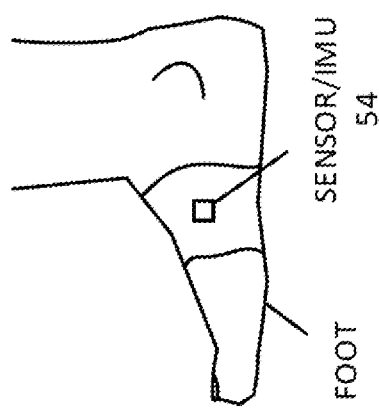
Figure 3A:
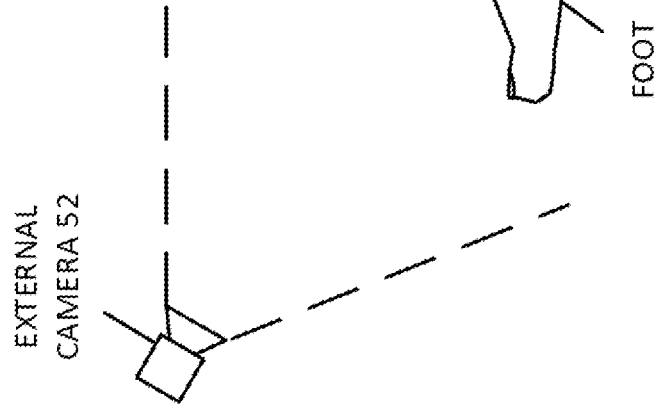

In one embodiment, FIG. 3B shows a foot pedal 50 having one or more sensors, additional proximity/hover sensors, and/or encoders that can sense a pressure input from a foot or a foot pedal position modified by the foot. Alternatively, a representation of the foot pedals can be projected onto the floor, e.g., from a 3D display or 3D head worn display. In one embodiment, as shown in FIG. 3C, the one or more foot input devices includes one or more tracking sensor(s) 54, e.g., an inertial measurement unit (IMU). The tracking sensors can include an accelerometer, a gyroscope, or combinations thereof. The sensors can be fixed to the foot (e.g., as a shoe, sock, stickers or straps) to detect movements of the foot. These inputs can be processed by the processor to toggle control between controllable members of the virtual surgical robotic system.

Sensed Hand and Foot Inputs

Figure 4:
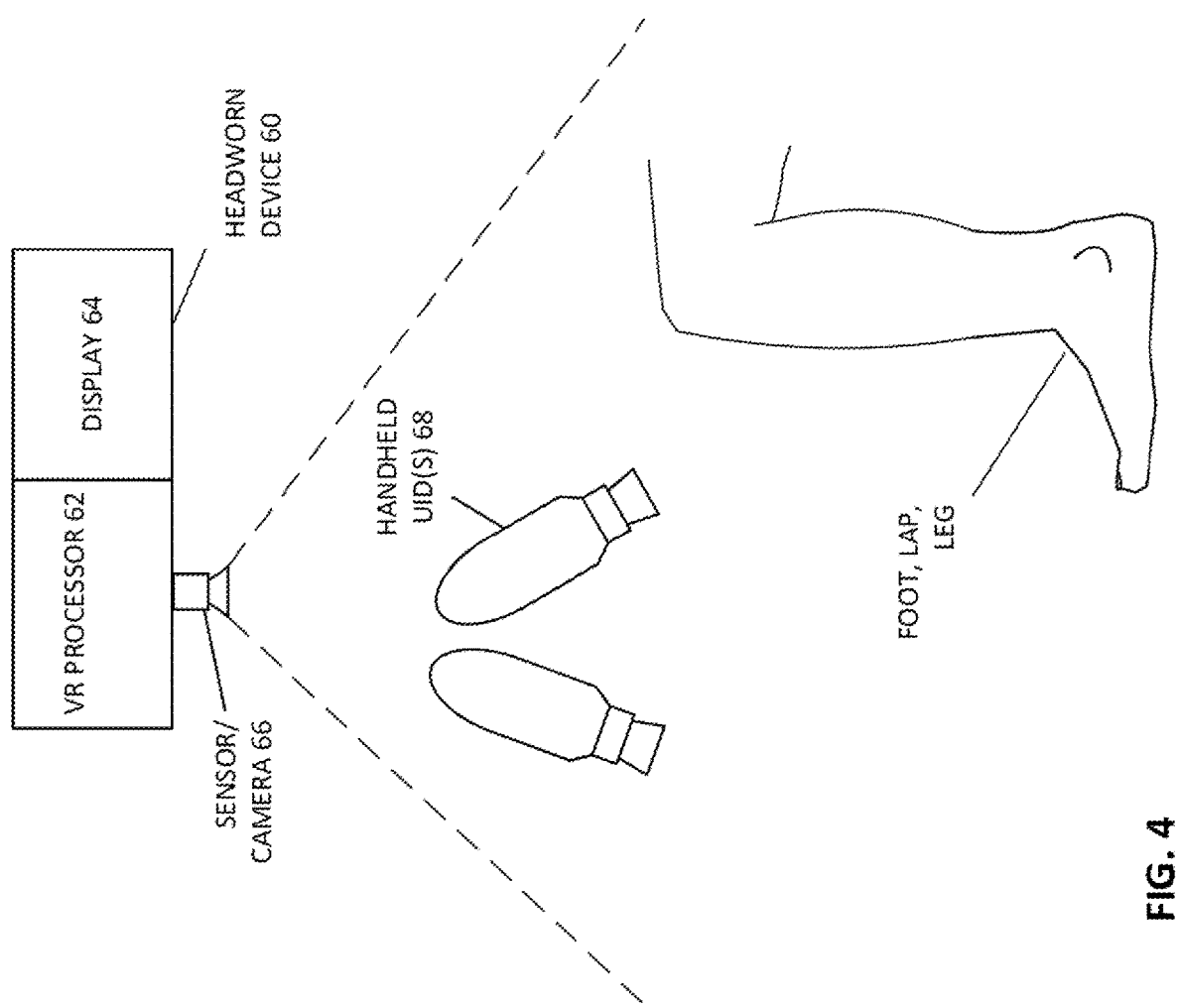
FIG. 4 illustrates a virtual reality system for simulation, training or demonstration of a surgical robotic system, according to one embodiment.

In one embodiment, a mobile virtual reality system for simulation, training or demonstration of a surgical robotic system, is shown in FIG. 4. The system can include: a virtual reality processor 62; a display 64, to receive and show a virtual reality environment generated by the processor. The virtual reality environment can include a) a virtual surgical robotic system (e.g., a system as shown in FIG. 1, in a virtual operating room), b) a means to receive a hand input from a hand, and c) a means to receive a foot input from a foot. The virtual reality processor can be configured to control a movement of the virtual surgical robotic system based on the hand input, and use foot motions and input to control other functions of the robotic system, such as switching between robotic instruments, endoscope, or arms of the virtual surgical robotic system.

In one embodiment, the system includes a camera or sensor 66, in communication with the processor, wherein the camera/sensor is positioned (e.g., located and oriented) to capture image data containing the hand input and the foot input from a user. The camera can communicate the image data to the processor (e.g., through a data bus, wires, network, etc.). The processor can be configured to identify the hand input by recognizing and tracking, in the image data, the hand or a handheld user interface device (UID) and to identify the foot input by recognizing and tracking, in the image data, a lap, a leg, and/or the foot and movements thereof.

In one embodiment, the processor can recognize the hand inputs by machine learning (e.g., one or more trained artificial neural network). For example, the processor can use object recognition and/or computer vision techniques to recognize and track console UIDs 68. In such a case, the console UIDs can be passive console UIDs without internal tracking elements (such as cameras or IMUs). Alternatively or additionally, the passive console UIDs can have one or more fiduciary markers (e.g., fixed on the surface of the console UID) and/or markings to help recognition and tracking of the console UID and positions and orientations thereof. Thus, the UIDs can beneficially be passive UIDs that do not require electronic power or communication with the processor. This can simplify the system for development and design, by placing the responsibility of hand inputs with the processor. This also can allow for dynamic programming of inputs, e.g., the processor can be programmed to receive new types of hand inputs without hardware redesign of the handheld UIDs.

In one embodiment, the system includes no additional sensors (e.g., cameras, foot pedals, buttons, etc.) to sense hand input and the foot input. Thus, no additional set-up of sensors would be required to provide a virtual training environment, improving the mobility of the system. In one embodiment, the processor, the camera, and the display are integral to a wearable device such as a head worn device 60, where the display is placed over the eyes, providing an immersive virtual experience. In one aspect, the camera is housed in a gimbal located on the wearable device.

Interface with Sectional Views

Figure 5:
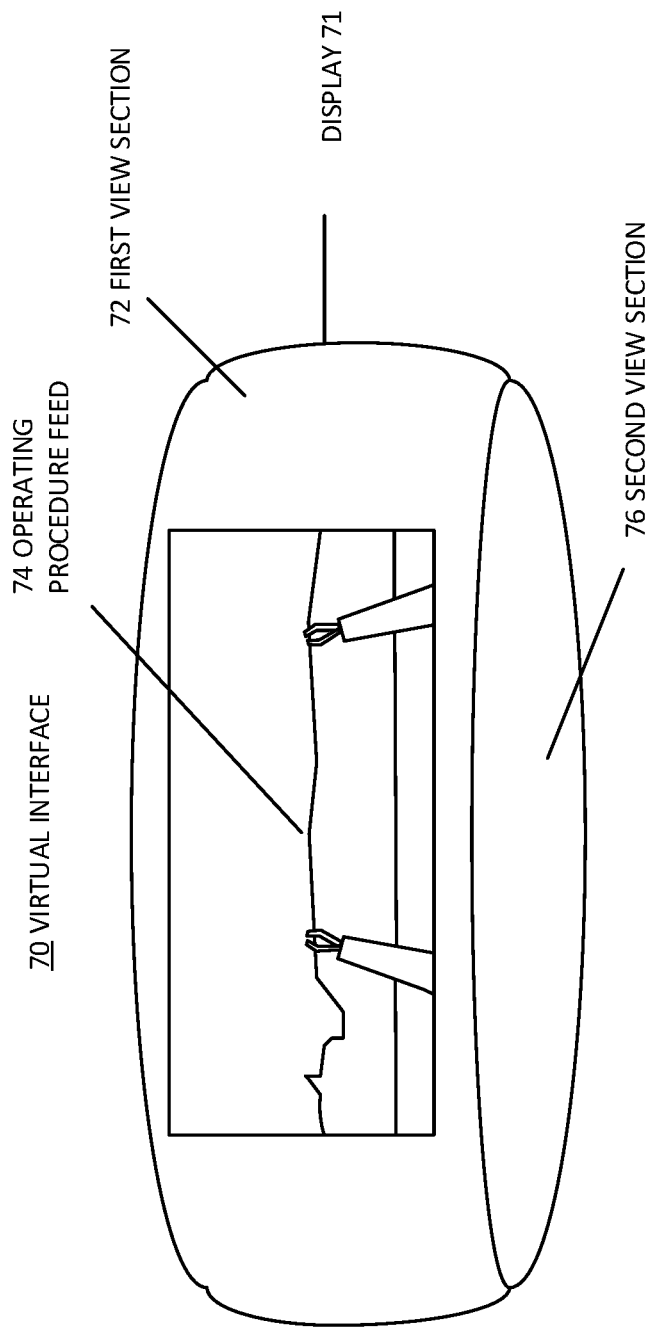
FIG. 5 shows a virtual interface, according to one embodiment.

In one aspect, as shown in FIG. 5, an immersive virtual interface 70 for simulation and teleoperation of a surgical robotic system, can include a display 71 having a first view section 72 showing a virtual view of an immersive operating procedure feed 74 and a second view section 76 showing user controls of the operating procedure. The operating procedure feed 74 can be a feed from a physical operating procedure (e.g., from cameras in a physical operating room), or a virtual operating procedure with virtual patient models and a virtual surgical robotic system (e.g., virtual surgical robotic arms, platform, patient model, etc.). The virtual interface can be integral to a head worn device where the display is worn over a user's eyes, providing an immersive visual and/or virtual environment. In one embodiment, one or more cameras of the head worn device can provide data for the second view section 76.

In one embodiment, the first view section and the second view section are rendered by a processor onto the display. For example, the second view can be a camera feed or virtual rendering. In one embodiment, the second view section has a camera feed showing physical pedals. Alternatively, the camera view can have augmented/virtual foot pedals rendered on the images from the camera feed. As mentioned, the camera feed can be generated by a camera of the head worn device (e.g., positioned to capture the body of the wearer of the device). In one embodiment, the second view section is a virtualized view, not of a camera feed. The virtualized view can be generated based on a camera feed and/or other sensor data. The virtualized view can show a virtual representation of a user's body, including feet. Virtual controls (e.g., virtual foot pedals) can be generated. In one embodiment, the user controls of the second view section include one or more of the following: foot pedals, a handheld user interface device, a user's feet, a user's hands. In one embodiment, virtual controls (e.g., virtual foot pedals, or virtual handheld UIDs) are generated in the user control view, rendered with the view of user's physical body. Beneficially, the user can see, through the user control view, the virtual controls being handled by the user's limbs, for improved control.

Alternatively, in one embodiment, the first view section is rendered onto the display by a processor, and the second view section includes an unobstructed opening of the display, the opening having a shape and size that permits a real work view of the user controls. The opening in the display is below the first view section or at the bottom portion of the display (e.g., towards a user's nose when the display is located over the eyes on a head worn device) and provides a view of the user's body and controls.

User Interface Flow

Figure 6:
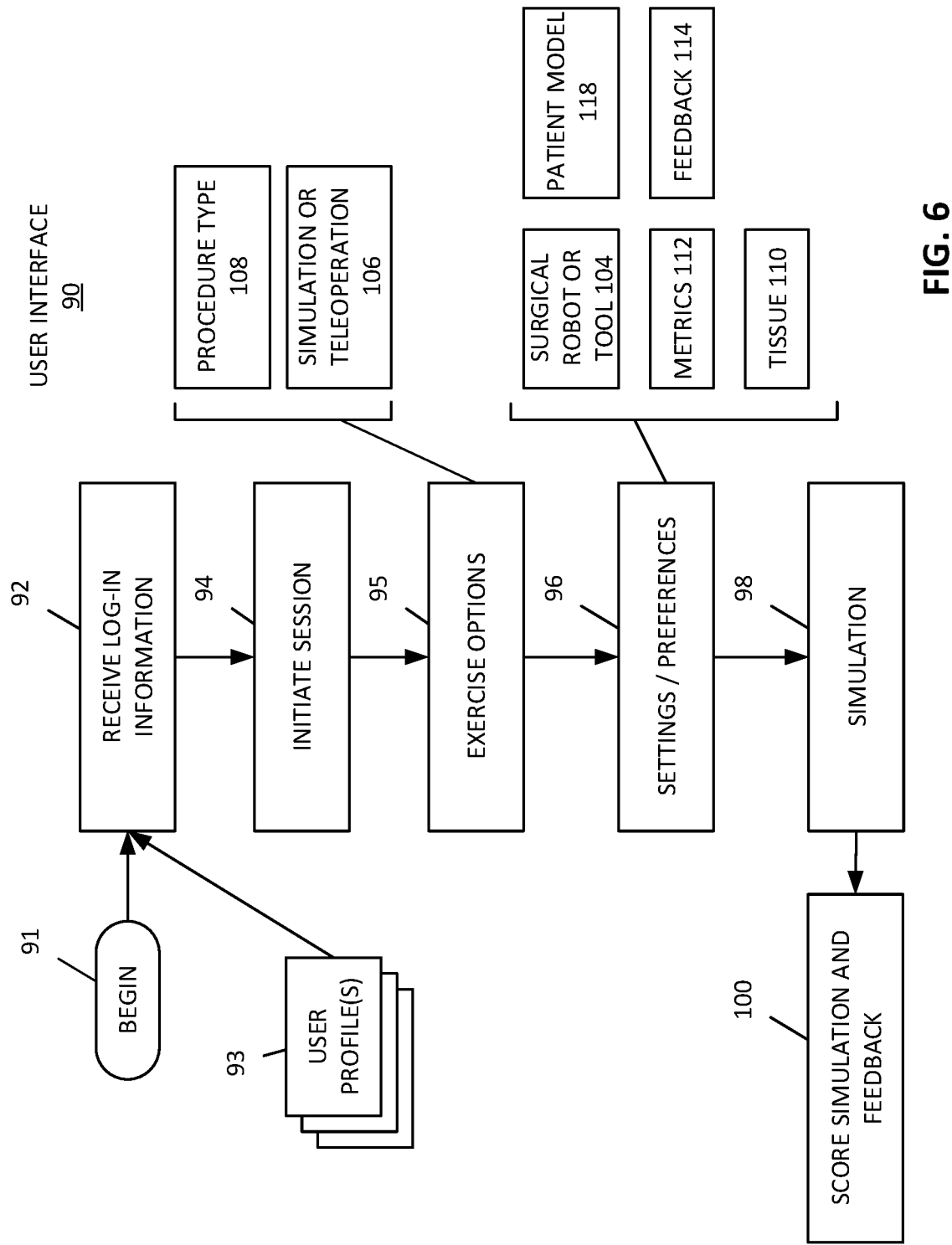
FIG. 6 shows a flow diagram of a user interface or process, according to one embodiment.

In FIG. 6, a user interface (or process performed by the user interface) 90 is shown for simulation and teleoperation of a surgical robotic system, according to one embodiment. The process can be initiated, for example, at block 91, by a user input such as a user picking up a handheld UID. The process can sense the pickup or movement of the UID, by techniques described in other sections of the disclosure. A display or screen (e.g., on a wearable device, laptop, or standalone monitor) can activate and turn on, in response to the initiation.

At block 92, the process can prompt a user for log-in information (e.g., with an input field) and/or receive a log-in information from a user. A user profile can be retrieved based on the log-in information. One or more user profiles 93 can be stored in a database and referenced when needed. Each user profile can have stored settings associated to the user profile. At block 94, the process can initiate a session, including syncing a user profile with the log-in information. In the case of a new user, a new user profile may be generated. The process can initiate a session based on the user log-in information.

At block 95, the process can provide selectable exercise options. In one embodiment, the process can present one or more options 106 of a) simulating one or more surgical procedures in a virtual environment and/or b) teleoperation of one or more surgical robotic procedures. Beneficially, the same log-in information and settings can be used for training and simulations of surgical robotic procedures, as well as real surgical robotic procedures. In one aspect, one or more exercises can be assigned to a user (e.g., by a second user or an automated dispatching system) through the user profile, the assigned exercises to be performed by the user of the user profile. Each exercise can specify a procedure type 108 (e.g., laparoscopic surgery of the abdomen). Thus, when a user logs in, the user can select from among the assigned exercises, for training/simulation and for real procedures. Updates and messages can also be presented based on user profile.

At block 96, the process can provide reconfigurable settings (e.g. preferences) of a surgical procedure. Such settings can include selecting equipment items of a surgical robotic system (e.g., a surgical robot type or tool type 104). Additionally, or alternatively, the equipment can be automatically selected based on the exercise (e.g., procedure type). In one aspect, a user can select one or more metrics 112 that will be measured during the simulation or teleoperation. In one embodiment, the settings can include tissue properties and interactions 110 (e.g., a thickness, softness, or strength of a tissue). In one aspect, the preferences/settings can include feedback types such as visual, auditory, and/or tactile feedback 114 such as showing a visual indication (e.g. highlighted on a display) of a surgical workspace, collisions and warnings of possible collisions, depth of a surgical tool in a patient or patient model, and tissue interactions. In one embodiment, the user can select a patient model 118 or model type (e.g., based on a patient size or shape/build). The process beneficially allows a user to select between different training simulations and gain proficiency with different surgical robotic models.

At block 98, the process can perform a simulated exercise of a surgical robotic procedure in a virtual environment (e.g., a surgical robotic system and patient model in a virtual operating room) or a teleoperation of a surgical robotic procedure through a live feed. The process can provide visual, auditory, or tactile feedback to the user during a simulated procedure, the feedback being provided for one or more of the following: a workspace (e.g., surgical workspace in a patient or patient model), faults, collisions, warnings, depth (e.g., depth of a surgical tool in a patient/model), tissue properties or interactions. The tactile or haptic feedback can be provided through one or more motors, vibrators and/or actuators, e.g. housed in a head-worn device or handheld UIDs. Visual feedback can be generated on a display. Auditory feedback can be generated through one or more speakers (e.g., located on a head worn device, standalone loudspeakers, or computer laptop speakers). The process and system 90 can be performed by a processor through a display (e.g., a head worn display, laptop, tablet, desktop computer, and other equivalent technology). In one embodiment, the user interface and process 90 is provided for the simulation and operation of the systems shown in FIGS. 1-5 (e.g., performed by the processors, displays, and UIDs mentioned therein).

In one embodiment, the process can, at block 100, determining a score and/or other feedback (e.g., exercise results, measured metrics, where a depth of the tool was exceeded, or where an incision may be too large) of the simulated surgical procedure. The score and other feedback can be provided to the user, e.g., through a user interface or display. In one embodiment, a user profile or data associated with the user profile can be updated based on the session (e.g., the settings/preferences of the session can be saved in association with the user profile).

In one embodiment, each of the systems shown in FIGS. 1-5 can form a mobile kit. For example, the handheld UIDs can be kitted (e.g., packaged) with a head worn device or laptop. The kit can provide a mobile training system or teleoperation for surgical robotic systems that can easily be shared between medical staff without requiring setup of external sensors that may be typical in a virtual reality system.

In one embodiment, the method includes displaying the virtual surgical environment. For example, the virtual surgical environment can be displayed to a user display on the user console (as shown in FIG. 1) or any display, local or remote. The virtual surgical environment can be displayed as a stadium view, plan view, first person view, or other view. The display can be driven by data transfer protocols between nodes (e.g., computing devices) on a network (e.g. TCP/IP, Ethernet, UDP, and more). In one embodiment, the virtual surgical environment is displayed to a head-mounted display. The wearer of the head-mounted display can be tracked such that the wearer can move throughout the virtual surgical environment to gain a three-dimensional understanding of the location and orientation of the various equipment as well as the unoccupied space and walkways within the virtual surgical environment. In one embodiment, the virtual surgical environment is interactive such that the user can adjust the orientation and/or location of objects in the virtual surgical environment (e.g., the virtual surgical robotic arm, the control tower, an angle or height of the surgical robotic platform, an angle of a display, and more).

In one embodiment, the processor(s) of the system (for example, a VR processor, robot controllers, cameras, displays, and robotic arms) can include a microprocessor and memory. Each processor may include a single processor or multiple processors with a single processor core or multiple processor cores included therein. Each processor may represent one or more general-purpose processors such as a microprocessor, a central processing unit (CPU), or the like. More particularly, each processor may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Each processor may also be one or more special-purpose processors such as an application specific integrated circuit (ASIC), a cellular or baseband processor, a field programmable gate array (FPGA), a digital signal processor (DSP), a network processor, a graphics processor, a communications processor, a cryptographic processor, a co-processor, an embedded processor, or any other type of logic capable of processing instructions.

Modules, components and other features, such as algorithms or method steps described herein can be implemented by microprocessors, discrete hardware components or integrated in the functionality of hardware components such as ASICS, FPGAs, DSPs or similar devices. In addition, such features and components can be implemented as firmware or functional circuitry within hardware devices, however, such details are not germane to embodiments of the present disclosure. It will also be appreciated that network computers, handheld computers, mobile computing devices, servers, and/or other data processing systems which have fewer components or perhaps more components may also be used with embodiments of the disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any particular programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A mobile virtual reality system for simulation, training or demonstration of a surgical robotic system, comprising:
   a processor;
   a display, to receive and show a virtual surgical robot from the processor, the virtual surgical robot including a plurality of virtual surgical instruments;
   one or more handheld user input devices (UIDs), sensing a hand input from a hand; and
   one or more foot input devices, comprising an optical sensor to capture visual data of a foot,
   wherein the processor is configured to
      control a movement of the virtual surgical robot based on the hand input,
      determine a foot input based on detecting a movement or position of the foot in the visual data, and
      change which of the virtual surgical instruments is controlled by the one or more handheld UIDs based on the foot input.

2. The mobile virtual reality system according to claim 1, wherein the mobile virtual reality system does not have an external stationary camera.

3. The mobile virtual reality system according to claim 1, wherein the processor and the display are integral to a laptop computer.

4. The mobile virtual reality system according to claim 1, wherein the display is a two-dimensional screen or a three-dimensional screen.

5. The mobile virtual reality system according to claim 1, wherein the display is a 3D wearable display, worn on a user's head.

6. The mobile virtual reality system according to claim 5, wherein the processor is integral with the display housed in a device.

7. The mobile virtual reality system according to claim 1, wherein the one or more handheld UIDs includes an inside-out tracking module and the processor is configured to determine the hand input based on data indicating movement, position, or orientation of the one or more handheld UIDs sensed by the inside-out tracking module.

8. The mobile virtual reality system according to claim 7, wherein the one or more handheld UIDs includes an inertial measuring unit (IMU), and the processor is configured to determine the hand input based on data indicating movement, position, or orientation of the one or more handheld UIDs sensed by the IMU.

9. The mobile virtual reality system according to claim 1, wherein the one or more foot input devices includes a foot pedal.

10. The mobile virtual reality system according to claim 1, wherein the one or more foot input devices includes tracking sensors.

11. The mobile virtual reality system according to claim 10, wherein the tracking sensors include an accelerometer, a gyroscope, or combinations thereof.

12. The mobile virtual reality system according to claim 1, wherein the processor is configured to detect and track the foot in the visual data by using machine learning.

13. The mobile virtual reality system according to claim 1, wherein the optical sensor includes a camera housed in the one or more handheld UIDs.

14. The mobile virtual reality system according to claim 13, wherein the camera has a field of view of 170° or greater, to capture the visual data containing the foot input.

15. A method for simulation of a surgical robotic system, comprising:
  presenting, to a display, a virtual surgical robot comprising a plurality of virtual surgical instruments;
  sensing a hand input from a hand with one or more handheld user input devices (UIDs); and
  sensing a foot input from a foot with one or more foot input devices, including capturing visual data of the foot with an optical sensor and detecting a movement or position of the foot in the visual data to determine the foot input,
  controlling a movement of the virtual surgical robot based on the hand input, and
  changing which of the virtual surgical instruments is controlled by the one or more handheld UIDs based on the foot input.

16. The method according to claim 15, wherein the surgical robotic system does not have an external stationary camera.

17. The method according to claim 15, wherein the display are integral to a laptop computer.

18. The method according to claim 15, wherein the display is a two-dimensional screen or a three-dimensional screen.

19. The method according to claim 15, wherein the display is a 3D wearable display, worn on a user's head.

20. The method according to claim 19, wherein the presenting the virtual surgical robot, the sensing the hand input, the sensing the foot input, the controlling the movement, and the changing are performed by at least one processor that is integral with the display housed in a device.

* * * * *